(12) United States Patent
Zinke et al.

(10) Patent No.: US 6,172,109 B1
(45) Date of Patent: Jan. 9, 2001

(54) 13-THIA PROSTAGLANDINS FOR USE IN GLAUCOMA THERAPY

(75) Inventors: Paul W. Zinke, Fort Worth; Mark R. Hellberg, Arlington, both of TX (US)

(73) Assignee: Alcon Laboratories, Inc., Fort Worth, TX (US)

( * ) Notice: Under 35 U.S.C. 154(b), the term of this patent shall be extended for 0 days.

(21) Appl. No.: 09/077,507

(22) PCT Filed: Mar. 6, 1998

(86) PCT No.: PCT/US98/04505

§ 371 Date: Mar. 11, 1999

§ 102(e) Date: Mar. 11, 1999

(87) PCT Pub. No.: WO98/39293

PCT Pub. Date: Sep. 11, 1998

Related U.S. Application Data

(60) Provisional application No. 60/040,051, filed on Mar. 7, 1997.

(51) Int. Cl.[7] ................................................. A61K 31/5575
(52) U.S. Cl. ........................................... 514/530; 562/428
(58) Field of Search ............................................... 514/530

(56) References Cited

U.S. PATENT DOCUMENTS

| 4,309,441 | 1/1982 | Radunz et al. . |
| 5,001,153 | 3/1991 | Ryuzo et al. . |
| 5,321,128 | 6/1994 | Stjernschantz et al. . |
| 5,516,796 | 5/1996 | Stjernschantz et al. . |
| 5,574,066 | 11/1996 | Chan et al. . |
| 5,578,618 | 11/1996 | Stjernschantz et al. . |
| 5,605,922 | * 2/1997 | DeSantis ............................... 514/392 |

FOREIGN PATENT DOCUMENTS

| 2513371 A1 | 10/1976 | (DE) . |
| 2550004 A1 | 5/1977 | (DE) . |
| WO 94/08585 | 4/1994 | (WO) . |
| WO 95/25520 | 9/1995 | (WO) . |
| WO 96/13267 | 5/1996 | (WO) . |
| WO 96/36599 | 11/1996 | (WO) . |
| WO 97/01534 | 1/1997 | (WO) . |

OTHER PUBLICATIONS

CA Selects: Prostaglandins, 125:185911P7, Issue 21, p. 3, 1996.
Merck Index, No. 5480 Luprostiol, 11 th Ed., p. 882.
Other Organics, B5, Wk. 9625, p. 12, KABI, 95–344451/44 (US 5516796–A).
Patent Abstracts of Japan: NDN 043–0088–2140–6: Prostaglandin Derivative, Publication No. 09286775 JP (Jan. 11, 1997).

* cited by examiner

*Primary Examiner*—Robert Gerstl
(74) *Attorney, Agent, or Firm*—Barry L. Copeland

(57) ABSTRACT

13-thia prostaglandins are useful in the treatment of glaucoma and ocular hypertension. Also disclosed are ophthalmic, pharmaceutical compositions comprising said prostaglandins.

11 Claims, No Drawings

13-THIA PROSTAGLANDINS FOR USE IN GLAUCOMA THERAPY

This application claims benefit to U.S. provisional application Ser. No. 60/040,051 filed Mar. 7, 1997.

BACKGROUND OF THE INVENTION

The present invention relates to the use of certain prostaglandin analogs for the treatment of glaucoma and ocular hypertension. As used herein, the terms "prostaglandin" and "PG" shall refer to prostaglandins and derivatives and analogs thereof, except as otherwise indicated by context.

Naturally-occurring prostaglandins, especially prostaglandins of the F series (such as $PGF_{2\alpha}$), are known to lower intraocular pressure (IOP) after topical ocular instillation, but can cause conjunctival hyperemia and/or edema as well as inflammation. Many synthetic prostaglandins have been observed to lower intraocular pressure, but most such compounds also produce the aforementioned side effects which significantly limit their clinical utility.

Various attempts have been made to overcome these well-known side-effects. Some have synthesized or searched out derivatives of naturally-occurring prostaglandins in an attempt to design out selectively the side effects while maintaining the IOP-lowering effect. See, e.g., Bishop et al. (U.S. Pat. No. 5,510,383) Stjernschantz et al. (U.S. Pat. Nos. 5,422,368, 5,321,128, and 5,296,504), Woodward et al. (U.S. Pat. No. 5,093,329), Chan et al. (WO 92/08465 and U.S. Pat. No. 5,446,041). Others, including Ueno et al. (EP 330 511 A2) and Wheeler (EP 435 682 A2) have tried complexing prostaglandins with various cyclodextrins.

Certain sulfur containing prostaglandin derivatives are known in the art. Glutathione-prostaglandin conjugates and related compounds have been reported in the literature relating to the cytotoxicity of PGA and PGD. See e.g. Cagen, Fales and Pisano, J. Biological Chemistry 251, 6550–54 (1976); Cagen and Pisano, Biochimica et Biophysica Acta 573, 547–51 (1979); Honn and Marnett, Biochemical and Biophysical Research Comn. 129, 34–40 (1985); Atsmon et al., Cancer Res. 50, 1879–85 (1990); Parker and Ankel, Biochemical Pharmacology 43,1053–60 (1992); Ohno, et al., Eicosanoids 5, 81–85 (1992). However, the biological effects of these compounds, other than cytotoxicity or the lack thereof, have not been reported. Stjernschantz et al. (U.S. Pat. No. 5,516,796) disclose ring substituted thioprostaglandins and thioprostagiandin-like compounds for the treatment of glaucoma or ocular hypertension. 7-Thioprostaglandin derivatives may inhibit chemokine-induced cell migration (Kataoka et al. (WO97/01534)) and have been disclosed for the treatment of skin disease (see Hanahima et al. CA Selects: Prostaglandins, 125:185911p (1996)). Also, compounds which are derivatives of 13-thiaprostenoic acid have been reported to lower blood pressure (see, e.g., Radunz et al. (U.S. Pat. No. 4,309,441)).

SUMMARY OF THE INVENTION

It has now been discovered that certain 13 thia analogs of $PGF_{2\alpha}$ will lower or control IOP with no or significantly reduced side effects of conjunctival hyperemia and/or edema. An agent which exhibits comparable efficacy, but with reduced side effects when compared to other agents, is said to have an improved therapeutic profile. While bound by no theories, the inventors believe that the 13-sulfur atom may act as a bioisostere of the 13,14-double bond of the normal prostaglandin omega chain. The present invention is believed to allow increased discrimination amongst the various PG receptors, which, in turn, allows a higher separation of desirable and undesirable activities, and therefore an improved therapeutic profile.

DETAILED DESCRIPTION OF THE INVENTION

The 13-thiaprostaglandins which are useful in the compositions of the present invention have the general formula (I):

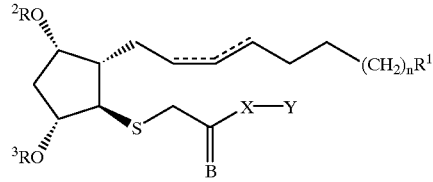

wherein:
  $R^1 = CO_2R$, $CONR^4R^5$, $CH_2OR^6$, or $CH_2NR^7R^8$;
    wherein:
    R=H or cationic salt moiety, or $CO_2R$ = pharmaceutically acceptable ester moiety;
    $R^4$, $R^5$ = same or different = H or alkyl; $R^6$ = H, acyl, or alkyl;
    $R^7$, $R_8$ = same or different = H, acyl, or alkyl; with the proviso that if one of $R^7$, $R^8$ = acyl then the other = H or alkyl;
  n=0 or 2
  $R^2$, $R^3$ = same or different = H, alkyl, or acyl;
  —=single or non-cumulated double bond;
  B=H, and OH in either configuration, H and F in either configuration, double bonded O, or $OCH_2CH_2O$;
  $X=(CH_2)_q$ or $(CH_2)_qO$; where q=1–6; and
  $Y=C_{1-6}$ alkyl group or phenyl ring optionally substitued with alkyl, halo, trihalomethyl, alkoxy, acyl, acyloxy, amino, alkyl amino, or hydroxy; or
  X-Y $(CH_2)_pY^1$; where p=0–6; and

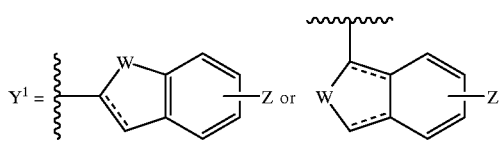

wherein:
  W=$CH_2$, O, $S(O)_m$, $NR^9$, $CH_2CH_2$, CH=CH, $CH_2O$, $CH_2S(O)_m$, CH=N, or $CHNR^9$; where m=0–2. and $R^9$=H, alkyl, or acyl;
  Z=H, alkyl, alkoxy, acyl, acyloxy, halo, trihalomethyl, amino, alkylamino, acylamino, or hydroxy; and
  —=single or double bond.

As used herein, the term "pharmaceutically acceptable ester" means any ester that would be suitable for therapeutic administration to a patient by any convential means without significant deleterious health consequences; and "ophthalmically acceptable ester" means any pharmaceutically acceptable ester that would be suitable for ophthalmic application i.e. non-toxic and non-irritating. Preferred are alkyl esters. Most preferred are $C_2$–$C_4$ alkyl esters and especially isopropyl esters.

Preferred compounds of the present invention are those of formula I wherein:

$R^1=CO_2R$; wherein R=alkyl;

$R^2$, $R^3$=H;

B=OH and H in either configuration;

X=$CH_2CH_2$ or $CH_2O$; and

Y=phenyl, optionally substitued with halo or trihalomethyl; or

X-Y=$(CH_2)_pY^1$; where p=0 and $Y^1$ = 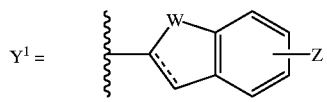

wherein:

W=$CH_2$, O, $S(O)_m$, $NR^9$, $CH_2CH_2$, CH=CH, $CH_2O$, $CH_2S(O)_m$, CH=N, or $CHNR^9$: where m=0–2. and $R^9$=H, alkyl, or acyl;

Z=H, alkyl, alkoxy, acyl, acyloxy, halo, trihalomethyl, amino, alkylamino, acylamino, or hydroxy; and ——=single or double bond.

Some of the above-mentioned prostaglandins are disclosed in U.S. Pat. No. 4,309,441 (Radunz et al.) and in German Patent No. 2,513,371 (Kraemer et al.). To the extent that such patents disclose the synthesis of the prostaglandin analogs of the present invention, they are incorporated by reference herein. Most preferred among the compounds that are generically or specifically disclosed in the art are:

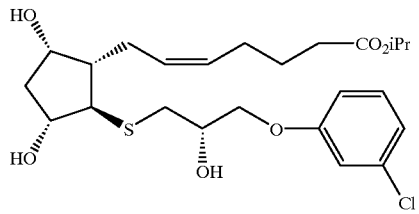

II. (5Z)-(9S, 11R, 15S)-9, 11, 15-trihydroxy-16-m-chlorophenoxy-13-thia-17, 18, 19, 20-tetranor-5-prostenoic acid isopropyl ester; and

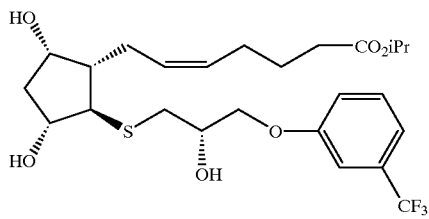

III. (5Z)-(9S, 11 R, 15S)9, 11, 15-trihydroxy-16-m-trifluoromethylphenoxy-13-thia-17, 18, 19, 20-tetranor-5-prostenoic acid isopropyl ester.

Others of the prostaglandins encompassed by the structure of formula (I) are believed to be novel. Specifically, those compounds possessing a cis double bond between carbons 4 and 5 in the α chain are believed to be novel. These compounds are represented by formula (IA):

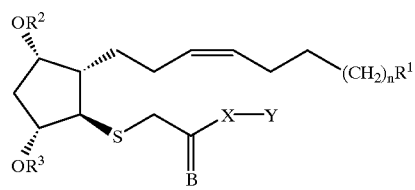

wherein all groups are as defined for formula (I). Most preferred among such cis $\Delta_4$ compounds is:

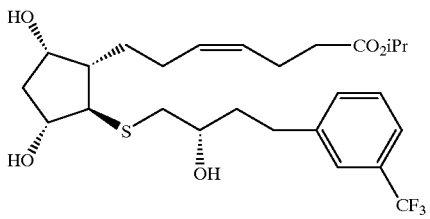

IV. (4Z)-(9S, 11R, 15S)9, 11,15-trihydroxy-16-m-trifluoromethylphenoxy-13-thia-17, 18, 19, 20-tetranor4-prostenoic acid isopropyl ester.

Also belielved to be novel are the 13-thia prostaglandins of formula (I) possessing a bicyclic ring at the terminus of the omega chain. Preferred among such bicyclic terminated compounds is:

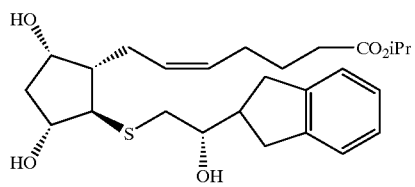

V. (5Z)-(9S, 11R, 15S)-9, 11, 15-trihydroxy-15-(2-indanyl)-13-thia-17, 18, 19, 20-tetranor-5-prostenoic acid isopropyl ester.

The compounds of formula (I) can be prepared by generally employing the methods disclosed in the foregoing references either alone or in combination with other known methods (e.g. those disclosed in U.S. Pat. No. 4,152,527 (Hess et al.)). The syntheses described in Examples 1–3 below are representative of those which may be used to prepare compounds of the present invention. Those skilled in the art will appreciate the modifications to the syntheses of the following Examples 1–3 necessary to yield such compounds. Those skilled in the art will further appreciate that the compounds of the present invention may exist in racemic, non-racemic, and enantiomerically pure forms which may be derived by conventional means. All such forms are within the scope of the present invention.

In the foregoing illustration, as well as those provided hereinafter, a hatched line, as used e.g. at carbon 9, indicates the α-configuration. A solid triangular line indicates the β-configuration. Dashed lines on bonds indicate a single or double bond. Two solid lines between carbons indicate a double bond of the specified configuration.

In the Examples which follow, the following standard abbreviations are used: g=grams (mg=milligrams); mol= moles (mmol=millimoles); mL=milliliters; mm Hg=millimeters of mercury; mp=melting point; bp=boiling point; d=days; h=hours; and min=minutes. In addition, "NMR" refers to nuclear magnetic resonance spectroscopy and "MS" refers to mass spectrometry.

EXAMPLE 1

Synthesis of (5Z)-(9S, 11R, 15S)-9, 11, 15-trihydroxy-16-m-chlorophenoxy-13-thia-17, 18, 19, 20-tetranor-5-prostenoic acid isopropyl ester (II).

A solution of (5Z)-(9S, 11R, 15S)-9, 11, 15-trihydroxy-16-m-chlorophenoxy-13-thia-17, 18, 19, 20-tetranor-5-prostenoic acid (0.0106 g, 0.024 mmol) (the synthesis of which is described in U.S. Pat. No. 4,309,441) in 3 mL of acetone was treated with DBU (0.015 g, 0.1 mmol) and 2-iodopropane (0.017 g, 0.1 mmol). The solution was stirred for 16 h at 23° C., then poured into dilute $NH_4Cl$ and extracted with ethyl acetate (2×50 mL). The combined organic extracts were dried over $MgSO_4$, filtered and concentrated in vacuo. The residue was purified by flash chromatography on silica gel 60 (230–400 mesh ASTM) with 5% $MeOH-CH_2Cl_2$ to furnish II (0.010 g, 89% yield), as a clear colorless oil, PMR ($CDCl_3$) $\delta7.21$ (m, 3H), 6.9 (m, 1H), 5.45 (m, 2H), 5.00 (hept., J=6.2 Hz, 1H), 4.2 (m, 3H), 2(4.02 (m, 2H), 3.05 (m, 1H), 2.9 (m, 1H), 2.8 (m, 2H), 2.4 (m, 2H), 2.3 (m, 1H), 2.1 (m, 2H), 1.9–1.5 (m, 6H), 1.24 (d, J=6.3 Hz, 6H). CMR ($CDCl_3$) $\delta179.61$, 159.17,134.94, 130.29, 130.24, 128.57, 121.43, 115.08, 113.09, 81.10, 73.46, 70.85, 69.51, 67.77, 56.96, 51.77, 41.67, 36.02, 34.01, 26.64, 26.17, 24.86, 21.83. Mass spectrum: 486.9, 468.9, 450.9, 233.0, 191.0, 167.5, 149.7.

EXAMPLE 2

Synthesis of (4Z)-(9S, 11R, 15S)-9, 11, 15-trihydroxy-16-m-trifluoromethylphenoxy-13-thia-17, 18, 19, 20-tetranor4-prostenoic acid isopropyl ester IV.

To 52 mL of a freshly prepared solution of 0.27 M sodium isopropoxide in isopropanol is added 2-hydroxy-3-(3-trifluoromethylphenoxy)propanethiol (2.62 g, 11.1 mmol) (U.S. Pat. No. 4,309,441) at room temperature. The resulting mixture is stirred for 1 h, and a solution of 7-(2-hydroxy4,5-cis-epoxy-cyclopent-1-yl)-hept-4-enoic acid isopropyl ester (1.5 g, 5.6 mmol) in isopropanol (10 mL) is added dropwise. The reaction mixture is stirred at room temperature for 5.5 h. Solid ammonium chloride is added to the mixture and the mixture is concentrated in vacuo. The residue is filtered through a pad of silica gel and the filter cake is washed several times with ethyl acetate. The combined washings are dried over magnesium sulfate, filtered, and the resulting solution is concentrated in vacuo.

The residue is purified by standard chromatography on silica get to provide samples of (4Z)-(9S, 11R, 15S)-9, 11, 15-trihydroxy-16-m-trifluoromethylphenoxy-13-thia-17, 18, 19, 20-tetranor4-prostenoic acid isopropyl ester (IV) and the undesired regioisomer.

The starting compound, 7-(2-hydroxy-4,5-cis-epoxy-cyctopent-1-yl)-hept4-enoic acid isopropyl ester can be prepared by the multiple step synthetic route shown in scheme 1. Reduction of the commercially available (−) cis-2-oxabicyclo[3.3.0]oct-6-en-3-one (1) in toluene at −78° C. using diisobutylaluminum hydride gives cis-2-oxabicyclo[3.3.0]oct-6-en-3-ol (2) which is used immediately without further purification. Wittig condensation of (2) with $Ph_3P^+CH_2OMe$ $Cl^-$ in the presence of potassium tert-butoxide yields the enol ether (3). Acidic hyrolysis using para-toluenesulfonic acid in tetrahydrofuran/water gives the lactol (4), which is reacted with $Ph_3P^+(CH_2)_3CO_2H$ $Br^-$ in the presence of potassium tert-butoxide in tetrahydrofuran. Treatment of an acetone solution of the resulting carboxylic acid (5) with DBU (1,8-diazobicyclo[5.4.0]undec-7-ene) and isopropyl iodide gives the ester. Selctive epoxidation of the cyclic double bond with $VO(acac)_2$ and tert-butyl hydroperoxide in methylene chloride at 0° C. gives the required starting material 7-(2-hydroxy4,5-cis-epoxy-cyclopent-1-yl)-hept-5-enoic acid isopropyl ester (6).

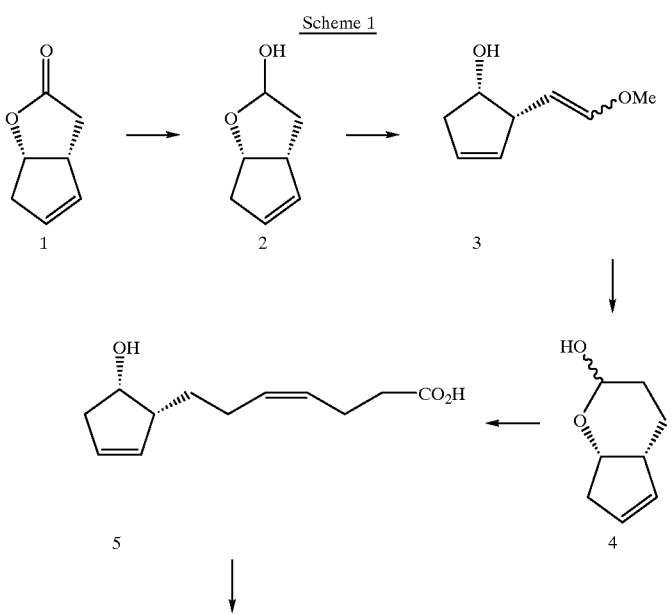

Scheme 1

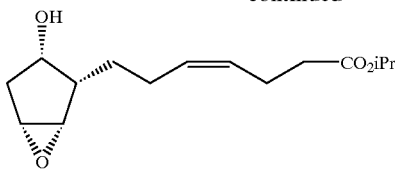

6

EXAMPLE 3

Synthesis of (5Z)-(9S, 11R, 15S)-9, 11, 15-trihydroxy-15-(2-indanyl)-13-thia-17, 18, 19, 20-tetranor-5-prostenoic acid isopropyl ester (V).

To 52 mL of a freshly prepared solution of 0.27 M sodium isopropxide in isopropanol is added 2-hydroxy-2-(indan-2-yl)ethanethiol (2.15 g, 11.1 mmol,) at room temperature. The resulting mixture is stirred for 1 h and a solution of 7-(2-hydroxy4,5-cis-epoxy-cyclopent-1-yl)-hept-5-enoic acid isopropyl ester (1.5 g, 5.6 mmol), (prepared by the method of U.S. Pat. No. 4,309,441 from commercially available (−) cis-2-oxabicyclo[3.3.0]oct-6-en-3-one ) in isopropanol (10 mL) is added dropwise. The reaction mixture is stirred at room temperature for 5.5 h. Solid ammonium chloride is added to the mixture and the mixture is concentrated in vacuo. The residue is filtered through a pad of silica gel and the filter cake is washed several times with ethyl acetate. The combined washings are dried over magnesium sulfate, filtered, and the resulting solution is concentrated in vacuo. The residue is purified by standard chromatography on silica gel to provide samples of (5Z)(9S, 11R, 15S)-9, 11, 15-trihydroxy-15-(2-indanyl)-13-thia-17, 18, 19, 20-tetranor-5-prostenoic acid isopropyl ester and the undesired regioisomer.

The starting compound, 2-hydrmxy-2-(indan-2-yl) ethanethiol (14) can be prepared by the multiple step synthetic route shown in scheme 2. Wittig condensation of the commercially available 2-indanone (7) with $Ph_3P^+CH_2OMe$ $Cl^-$ in the presence of potassium tert-butoxide yields the enol ether (8). Acidic hydrolysis using para-toluenesulfonic acid in tetrahydrofuran/water gives the aldehyde (9). Wittig condensation of the aldehyde (9) with $Ph_3PCH_2$ gives the olefin (10). Sharpless asymmetric dihydroxylation with $(DHQ)_2PHAL$ (1,4-phthalazinediyl diether hydroquinone) (Sharpless et al., *The Osmium-Catalyzed Asymmetric Dihydroxylation: A New Ligand Class and a Process Improvement, J. Org. Chem.,* volume 57, pages 2768–2771 (1992)) provides the diol (11) which is converted to the monotosylate (12) by treatment with para-toluenesulfonyl chloride and pyridine in diethyl ether. The tosylate (12) is reacted with sodium methoxide in methanol to give the epoxide (13). Reaction of the epoxide (13) with thioacetic acid followed by the reduction of the thioester with lithium aluminum hydride gives the starting compound (14).

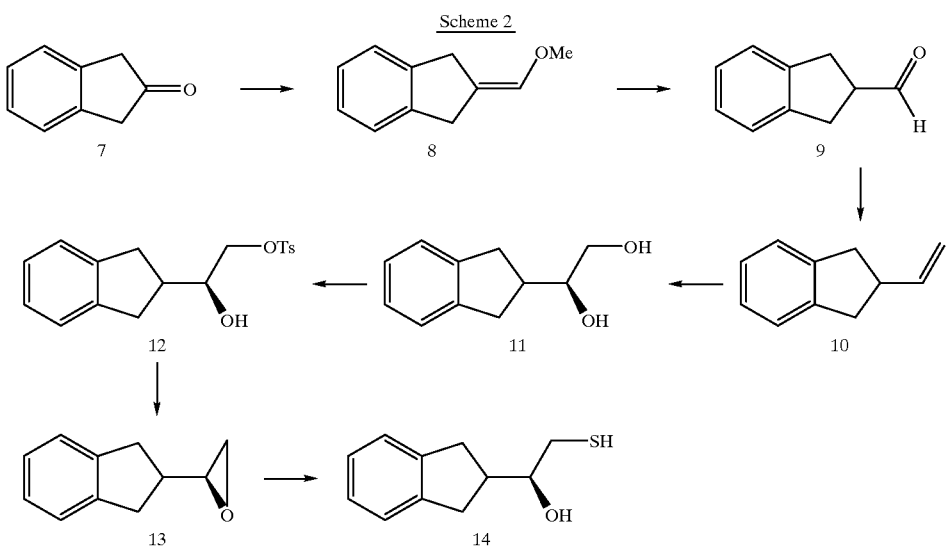

Scheme 2

The 13-thia prostaglandins of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention may be administered as solutions, suspensions, or emulsions (dispersions) in an ophthalmically acceptable vehicle. As used herein, the term "ophthalmically acceptable vehicle" refers to any substance or combination of substances which are effectively non-reactive with the compounds and suitable for administration to a patient. Stabilizers and/or solubilizers are not considered to be reactive substances. Preferred are aqueous vehicles suitable for topical application to the patient's eyes.

The compounds of the present invention are preferably administered topically. The dosage range is generally between about 0.01 and about 1000 micrograms per eye (µg/eye) and is preferably between about 0.1 and 100 µg/eye. In forming compositions for topical administration, the compounds of the present invention are generally formulated as between about 0.001 to about 1.0 percent by weight (wt %) solutions in water at a pH between about 4.5 to 8.0 and preferably between about 7.0 and 7.5. The compounds are preferably formulated as between about 0.0001 to about 0.1 wt % and, most preferably, between about 0.001 and about 0.02 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents and viscosity building agents.

Antimicrobial Preservatives:

Ophthalmic products are typically packaged in multidose form.

Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents:

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; cyclodextrin; CREMOPHORE® EL (polyoxyl 35 castor oil); or other agents known to those skilled in the art. Such co-solvents are typically employed at a level between about 0.01 % and about 2% by weight.

Viscosity Agents:

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight.

The following examples are representative pharmaceutical compositions of the invention for topical use in lowering of intraocular pressure.

EXAMPLE 4

The following formulations A–E are representative pharmaceutical compositions of the invention for topical use in lowering of intraocular pressure. Each of formulations A through E may be formulated in accordance with procedures known to those skilled in the art.

| FORMULATION A | |
|---|---|
| Ingredient | Amount (wt %) |
| Compound of formula II | 0.01 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCl and/or NaOH | pH 7.2–7.5 |
| Purified water | q.s. to 100% |

| FORMULATION B | |
|---|---|
| Ingredient | Amount (wt %) |
| Compound of formula III | 0.03 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.01 |
| Benzalkonium chloride | 0.02 |
| Polysorbate 80 | 0.15 |
| HCl and/or NaOH | pH 7.3–7.4 |
| Purified water | q.s. to 100% |

| FORMULATION C | |
|---|---|
| Ingredient | Amount (wt %) |
| Compound of formula IV | 0.01 |
| Dextran 70 | 0.1 |
| Hydroxypropyl methylcellulose | 0.5 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Benzalkonium chloride | 0.01 |
| NaOH and/or HCl | pH 7.3–7.4 |
| Purified water | q.s. to 100% |

| FORMULATION D | |
|---|---|
| Ingredient | Amount (wt %) |
| Compound of formula V | 0.03 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Benzalkonium chloride | 0.01 |
| HCl and/or NaOH | pH 7.3–7.4 |
| Purified water | q.s. to 100% |

FORMULATION E

| Ingredient | Amount (wt/vol %) |
| --- | --- |
| Compound of formula II | 0.01 |
| Polyoxyl 35 castor oil | 0.1 |
| Tromethamine | 0.12 |
| Boric acid | 0.3 |
| Mannitol | 4.6 |
| Disodium EDTA (edetate disodium) | 0.1 |
| Benzalkonium Chloride Solution | 0.01 |
| HCl and/or NaOH | pH 7.3–7.4 |
| Purified Water | q.s. to 100% |

EXAMPLE 5

Compound II and PGF$_{2\alpha}$ isopropyl ester (PGF$_{2\alpha}$ iPr) were tested for ocular irritation in the New Zealand (NZA) rabbit. The prostaglandins were administered in 30 μL of test formulation. Conjunctival hyperemia, swelling and discharge were evaluated using a system devised to grossly compare the irritation potential of prostaglandins in the NZA rabbit. Using the Hackett/McDonald scoring system (Hackett, R. B. and McDonald, T. O. "Eye Irritation" in *Dermatotoxicology*, 4th edition, Marzulli, F. N. and Maibach, H. I. editors, Hemisphere Publishing Corp., Washington D.C. (1991)), conjunctival hyperemia, conjunctival swelling, and ocular discharge were graded using a slit-lamp prior to compound instillation and 1, 2, 3, and 5 hours after topical ocular instillation of the test compound. The percentage of eyes scoring +2 or greater for all time points was calculated for each parameter (conjunctival hyperemia, conjunctival swelling, and ocular discharge). To facilitate comparison, PGF$_{2\alpha}$ iPr was administered at the same time as the test agent. The cumulative results are presented in Table 1.

TABLE 1

| | | % Incidence | | |
| --- | --- | --- | --- | --- |
| Compound | Number of Animals | Hyperemia | Conjunctival Swelling | Discharge |
| II (3 μg) | 10 | 0 | 30 | 0 |
| II (10.0 μg) | 10 | 23 | 33 | 5 |
| PGF$_{2\alpha}$iPr (1.0 μg) | 10 | 58, 58 | 67, 63 | 47, 48 |

It is evident from Table 1 that the 13-thia analog of PGF$_{2\alpha}$ isopropyl ester, compound 11, produced a low incidence of ocular irritation in the rabbit compared to PGF$_{2\alpha}$ isopropyl ester, which caused a relatively high incidence of hyperemia, conjunctival swelling and discharge. This indicates that the structural modification present in compound II attenuates the ocular side effects associated with the PGF$_{2\ \alpha}$ isopropyl ester.

EXAMPLE 6

Compound II and PGF$_{2\alpha}$ isopropyl ester (PGF$_{2\alpha}$ iPr) were tested for IOP-lowering effect in cynomologus monkey eyes. The right eyes of the cynomologus monkeys in this study were previously given laser trabeculoplasty to induce ocular hypertension in the lasered eye. Animals had been trained to sit in restraint chairs and conditioned to accept experimental procedures without chemical restraint. IOP was determined with a pneumatonometer after light corneal anesthesia with dilute proparacaine. The test protocol included a five-dose b.i.d. treatment regimen because of the typical delayed response to prostaglandins. The test formulations were administered to the lasered right eyes, and the normal left eyes remained untreated for compound 11, or to both eyes for PGF$_{2\alpha}$ isopropyl ester (PGF$_{2\alpha}$ iPr). Baseline IOP values were determined prior to treatment with the test formulation, and IOP was determined 16 hours after the fourth dose for all compounds, 2, 4, and 6 hours after the fifth dose for compound II, and 1, 3 and 7 hours after the fifth dose for PGF$_{2\alpha}$ iPr. Results are presented in Table 2 as the mean percent reduction of IOP from baseline +/- SEM. Prostaglandins were administered in 30 μL of test formulation.

TABLE 2

| | Number of Animals | Baseline IOP (mm/Hg) | Percent IOP Reduction +/-SEM (Hours after Last Dose/Dose #) | | | | | | |
| --- | --- | --- | --- | --- | --- | --- | --- | --- | --- |
| Compound | | | 16/4 | 1/5 | 2/5 | 3/5 | 4/5 | 6/5 | 7/5 |
| II (3.0 μg) | 9 | 32.2 | 18.0 +/- 3.0 | | 23.3 +/- 3.5 | | 24.2 +/- 3.6 | 24.9 +/- 3.4 | |
| II (1.0 μg) | 9 | 31.6 | 4.6 +/- 6.1 | | 13.9 +/- 6.8 | | 8.1 +/- 6.6 | 10 +/- 6.2 | |
| PGF$_{2\alpha}$ iPr 1.0 μg) | 4 | 34.8 | 5.8 +/- 4.0 | 27.6 +/- 14.4 | | 38 +/- 1.7 | | | 25.6 +/- 14.4 |

Table 2 shows that compound II, produces a significant degree of IOP reduction for the time period tested. Thus, the 13-thia prostaglandin compound II, with a low incidence of side effects (Example 5), exhibits a significantly improved therapeutic profile over PGF$_{2\alpha}$ isopropyl ester.

The invention has been described by reference to certain preferred embodiments however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma and ocular hypertension which comprises administering to the affected eye a therapeutically effective amount of a compound of formula (I):

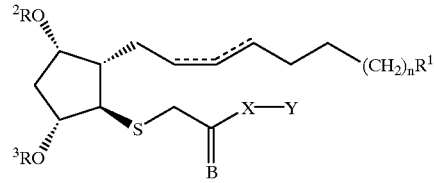

wherein:
R$^1$=CO$_2$R, CONR$^4$R$^5$, CH$_2$OR$^6$, or CH$_2$NR$^7$R$^8$;
wherein:

R=H or cationic salt moiety, or CO$_2$R= pharmaceutically acceptable ester moiety;

R$^4$, R$^5$=same or different=H or alkyl; R$^6$=H, acyl, or alkyl;

R$^7$, R$^8$=same or different=H, acyl, or alkyl; with the proviso that if one of R$^7$, R$^8$=acyl then the other=H or alkyl;

n=0 or 2;

R$^2$, R$^3$=same or different=H, alkyl, or acyl;

B=H, and OH in either configuration, H and F in either configuration, double bonded O, or OCH$_2$CH$_2$O;

X=(CH$_2$)$_q$ or (CH$_2$)$_q$O; where q=1–6; and

Y=C$_{1-6}$ alkyl group or phenyl ring optionally substituted with alky, halo, trihalomethyl, alkoxy, acyl, acyloxy, amino, alkyl amino, or hydroxy; or X-Y=(CH$_2$)$_p$Y$^1$; where p=0–6; and

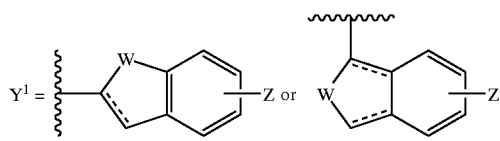

or wherein:

W=CH$_2$, O, S(O)$_m$, NR$^9$, CH$_2$CH$_2$, CH=CH, CH$_2$O, CH$_2$S(O)$_m$, CH=N, or CHNR$^9$; where m=0–2, and R$^9$=H, alkyl, or acyl;

Z=H, alkyl, alkoxy, acyl, acyloxy, halo, trihalomethyl, amino, alkylamino, acylamino, or hydroxy; and —=single or double bond;

with the proviso that the following compounds are excluded: [1 S-[1α(Z),2β(R*),3α,5α]]-7-[2-[[3-(3-Chlorophenoxy)-2-hydroxypropyl]thiol]-3,5-dihydroxycyclopentyl]-5-heptenoic acid and pharmaceutically acceptable esters and salts thereof.

2. The method of claim 1, wherein the compound is administered topically.

3. The method of claim 2, wherein between about 0.01 and about 1000 micrograms of the compound is administered.

4. The method of claim 3, wherein between about 0.1 and about 100 micrograms of the compound is administered.

5. The method of claim 1, wherein for the compound of formula I:

R$^1$=CO$_2$R; wherein R=alkyl;

R$^2$, R$^3$=H;

B=OH and H in either configuration;

X=CH$_2$CH$_2$ or CH$_2$O; and

Y=phenyl, optionally substituted with halo or trihalomethyl; or

X-Y=(CH$_2$)$_p$Y$^1$; where p=0 and

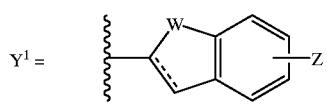

wherein:

W=CH$_2$, O, S(O)$_m$, NR$^9$, CH$_2$CH$_2$, CH=CH, CH$_2$O, CH$_2$S(O)$_m$, CH=N, or CHNR$^9$; where m=0–2, and R$^9$=H, alkyl, or acyl;

Z=H, alkyl, alkoxy, acyl, acyloxy, halo, trihalomethyl, amino, alkylamino, acylamino, or hydroxy; and —=single or double bond;

with the proviso that the following compounds are excluded: [1S-[1α(Z),2β(R*),3α,5α]]-7-[2-[[3-(3-Chlorophenoxy)-2-hydroxypropyl]thio]-3,5-dihydroxycyclopentyl]-5-heptenoic acid and pharmaceutically acceptable esters and salts thereof.

6. The method of claim 5, wherein the compound of formula I is:

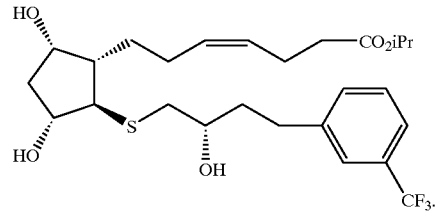

7. The method of claim 5, wherein the compound of formula I is:

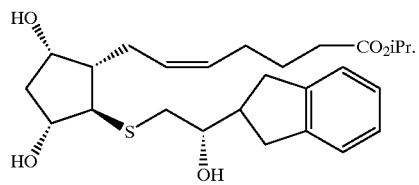

8. The method of claim 5, wherein for the compound of formula I: R=isopropyl, B=OH in the alpha configuration and H in the beta configuration, X=CH$_2$O. and Y=phenyl substituted with Cl or trifluoromethyl.

9. The method of claim 5, wherein the compound is administered topically.

10. A topical ophthalmic composition for the treatment of glaucoma and ocular hypertension, said composition comprising an ophthalmically acceptable vehicle and a therapeutically effective amount of a compound of formula (I):

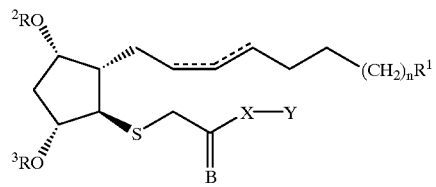

wherein:

R$^1$=CO$_2$R, CONR$^4$R$^5$, CH$_2$OR$^6$, or CH$_2$NR$^7$R$^8$; wherein:

R=H or cationic salt moiety, or CO$_2$R= pharmaceutically acceptable ester moiety;

R$^4$, R$^5$=same or different=H or alkyl; R$^6$=H, acyl, or alkyl;

R$^7$, R$^8$=same or different=H, acyl, or alkyl; with the proviso that if one of R$^7$, R$^8$=acyl then the other=H or alkyl;

n=0 or 2;

R$^2$, R$^3$=same or different=H, alkyl, or acyl;

—=single or non-cumulated double bond;

B=H, and OH in either configuration, H and F in either configuration, double bonded O, or OCH$_2$CH$_2$O;

$X=(CH_2)_q$ or $(CH_2)_qO$; where q=1–6; and $Y=C_{1-6}$ alkyl group or phenyl ring optionally substituted with alkyl, halo, trihalomethyl, alkoxy, acyl, acyloxy, amino, alkyl amino, or hydroxy; or $X-Y=(CH_2)_pY^1$; where p=0–6; and

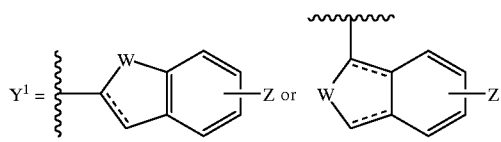

or wherein:

W=$CH_2$, O, $S(O)_m$, $NR^9$, $CH_2CH_2$, CH=CH, $CH_2O$, $CH_2S(O)_m$, CH=N, or $CHNR^9$; where m=0–2, and $R^9$=H, alkyl, or acyl;

Z=H, alkyl, alkoxy, acyl, acyloxy, halo, trihalomethyl, amino, alkylamino, acylamino, or hydroxy; and —=single or double bond;

with the proviso that the following compounds are excluded: [1S-[1α(Z),2β(R*),3α,5α]]-7-[2-[[3-(3-Chlorophenoxy)-2-hydroxypropyl]thio]-3,5-dihydroxycyclopentyl]-5-heptenoic acid and pharmaceutically acceptable esters and salts thereof.

11. A method of treating glaucoma and/or ocular hypertension which comprises administering to the affected eye a therapeutically effective amount of a composition consisting essentially of a compound of formula (I):

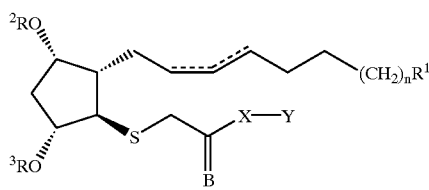

wherein:

$R^1=CO_2R$, $CONR^4R^5$, $CH_2OR^6$, or $CH_2NR^7R^8$; wherein:

R=H or cationic salt moiety, or $CO_2R$=pharmaceutically acceptable ester moiety;

$R^4$, $R^5$=same or different=H or alkyl; $R^6$=H, acyl, or alkyl;

$R^7$, $R^8$=same or different=H, acyl, or alkyl; with the proviso that if one of $R^7$, $R^8$=acyl then the other=H or alkyl;

n=0 or 2;

$R^2$, $R^3$=same or different=H, alkyl, or acyl;

B=H, and OH in either configuration, H and F in either configuration, double bonded O, or $OCH_2CH_2O$;

$X=(CH_2)_q$ or $(CH_2)_qO$; where q=1–6; and $Y=C_{1-6}$ alkyl group or phenyl ring optionally substituted with alkyl, halo, trihalomethyl, alkoxy, acyl, acyloxy, amino, alkyl amino, or hydroxy; or $X-Y=(CH_2)_pY^1$; where p=0–6; and

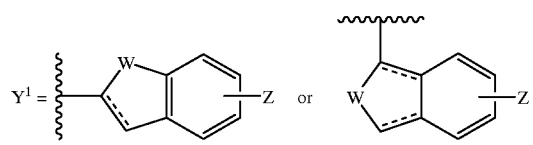

wherein:

W=$CH_2$, O, $S(O)_m$, $NR^9$, $CH_2CH_2$, CH=CH, $CH_2O$, $CH_2S(O)_m$, CH=N, or $CHNR^9$; where m=0–2, and $R^9$=H, alkyl, or acyl;

Z=H, alkyl, alkoxy, acyl, acyloxy, halo, trihalomethyl, amino, alkylamino, acylamino, or hydroxy; and —=single or double bond; and an ophthalmically acceptable vehicle therefor.

* * * * *